US012406756B2

(12) United States Patent
Maslowski et al.

(10) Patent No.: US 12,406,756 B2
(45) Date of Patent: Sep. 2, 2025

(54) ARTIFICIAL INTELLIGENCE BOOSTING DOSE CALCULATIONS

(71) Applicant: Siemens Healthineers International AG, Steinhausen (CH)

(72) Inventors: Alexander Maslowski, Peachtree City, GA (US); Douglas Allen Barnett, Palo Alto, CA (US); Todd Wareing, Palo Alto, CA (US)

(73) Assignee: Siemens Healthineers International AG, Steinhausen (CH)

( * ) Notice: Subject to any disclaimer, the term of this patent is extended or adjusted under 35 U.S.C. 154(b) by 87 days.

(21) Appl. No.: 17/692,091

(22) Filed: Mar. 10, 2022

(65) Prior Publication Data

US 2023/0290465 A1 Sep. 14, 2023

(51) Int. Cl.
*G16H 20/10* (2018.01)
*G06N 3/08* (2023.01)
*G06V 10/82* (2022.01)

(52) U.S. Cl.
CPC ............ *G16H 20/10* (2018.01); *G06N 3/08* (2013.01); *G06V 10/82* (2022.01)

(58) Field of Classification Search
CPC ........... G16H 20/10; G06V 10/82; G06N 3/08
See application file for complete search history.

(56) References Cited

U.S. PATENT DOCUMENTS

| | | | | |
|---|---|---|---|---|
| 10,726,587 B2* | 7/2020 | Zhao | ................... | G06T 3/4076 |
| 2007/0049785 A1* | 3/2007 | Pekar | ................... | A61N 5/1049 |
| | | | | 600/1 |
| 2011/0106562 A1* | 5/2011 | Gogineni | ............... | G16H 20/40 |
| | | | | 705/3 |
| 2013/0090549 A1* | 4/2013 | Meltsner | ............... | A61N 5/1042 |
| | | | | 600/1 |
| 2016/0303398 A1* | 10/2016 | Eriksson | ............... | A61N 5/1031 |
| 2017/0337682 A1 | 11/2017 | Liao et al. | | |
| 2019/0192880 A1* | 6/2019 | Hibbard | ................. | G06N 3/045 |
| 2019/0348256 A1* | 11/2019 | Geurts | .................... | G06T 7/254 |
| 2020/0254277 A1* | 8/2020 | Eriksson | ............... | A61N 5/1039 |
| 2021/0265057 A1 | 8/2021 | Karanam et al. | | |
| 2022/0192619 A1* | 6/2022 | Sun | ........................ | A61B 5/055 |
| 2022/0309650 A1* | 9/2022 | Vija | ..................... | G06T 7/0012 |

(Continued)

FOREIGN PATENT DOCUMENTS

EP         4124359 A1 *  2/2023   ............. A61B 6/466

OTHER PUBLICATIONS

Borgers, Christoph, Complexity of Monte Carlo and Deterministic Dose-Calculation Methods, 1998, Physics in Medicine & Biology, 43, 517 (Year: 1998).*

(Continued)

*Primary Examiner* — Matthew L Hamilton
(74) *Attorney, Agent, or Firm* — Foley & Lardner LLP

(57) ABSTRACT

Embodiments described herein provide for training an artificial intelligence model to boost dose depositions. The artificial intelligence model receives medical images and a dose deposition determined according to a first dose deposition model. The artificial intelligence model modifies the received dose deposition determined according to the first dose deposition model such that the dose deposition simulates a dose deposition determined by a second dose deposition model.

18 Claims, 4 Drawing Sheets

(56) References Cited

U.S. PATENT DOCUMENTS

2023/0128148 A1* 4/2023 Li ........................ A61N 5/1036
600/1
2024/0001149 A1* 1/2024 Zhao ...................... G16H 20/40

OTHER PUBLICATIONS

Ma, C-M, A Monte Carlo Dose Calculation Tool for Radiotherapy Treatment Planning, 2002, Physics in Medicine & Biology, 47, 1671 (Year: 2002).*

International Search Report and Written Opinion on PCT App. PCT/US2023/013940 dated Jun. 16, 2023 (11 pages).

International Preliminary Report on Patentability and Written Opinion on International Application No. PCT/US2023/013940 dated Sep. 10, 2024 (5 pages).

* cited by examiner

ARTIFICIAL INTELLIGENCE BOOSTING DOSE CALCULATIONS

TECHNICAL FIELD

This application relates generally to modeling dose deposition for radiotherapy treatment.

BACKGROUND

Radiation therapy is a localized treatment using ionizing radiation for a specific target tissue, such as a cancerous tumor. Ideally, radiation therapy is performed on target tissue (also referred to as the planning target volume) that spares the surrounding normal tissue from receiving doses above specified tolerances, thereby minimizing the risk of secondary toxicities from damage to healthy tissue. Due to the strong biological impact of the ionizing radiation emitted from a radiation therapy machine, it is imperative that treatment directives are precisely calculated and followed. Treatment directives (also referred to as treatment attributes) may refer to various directives of how a patient's treatment is implemented, including attributes of a radiation therapy machine while the patient is receiving the prescribed radiotherapy dose and how the dosage is delivered to the patient's organs. For instance, the prescribing physician may identify a source location (e.g., patient's organ to be treated or tumor to be eradicated) and a corresponding dosage. These treatment directives may be stored as part of a radiation therapy treatment plan (RTTP).

Various radiotherapy treatments (e.g., very high energy electrons, magnetic resonance linear accelerators, traditional electron treatments, small target for photon treatments, cone treatments, etc.) have complex beam geometries. Generally, determining how the dosage is delivered to the patient's tissue can be sub-divided into at least two tasks: (1) modeling the radiation produced by a linear accelerator providing the radiation therapy (e.g., source modeling), and (2) calculating/modeling the dosage received by the patient (e.g., the dose deposition). The simulated behavior of the radiation (source model) is imported into its downstream models to calculate the dose received by the patient. Inaccuracies in the source modeling may propagate to inaccuracies in the dosage calculations.

In some conventional implementations, nondeterministic probabilistic methods such as Monte Carlo (MC) simulations can simulate how radiation behaves. MC simulations statistically estimate multiple possible outcomes of particular events (e.g., particle location, energy, direction, etc.) by simulating random repeated sampling of each particle. In other implementations, finite element methods, finite volume methods, and other deterministic methods may be performed to simulate how radiation behaves. Nondeterministic methods and deterministic methods may trade speed and accuracy. For instance, MC simulations may achieve higher accuracy simulations of radiation behavior than deterministic methods because convergence for MC depends on a number of particle-histories simulated, not on mesh refinement (or the number of features) in a computed tomography image. The simulation of many events for many particles implies that MC simulations are too slow for clinical applications, although these solutions are accurate because they do not depend on features of an image. In contrast, deterministic methods may converge to a radiation behavior solution faster than MC simulations by simulating the behavior of the entire statistical populations of particles and events. Accordingly, deterministic methods consume less computational power and have a reduced run-time, but may be less accurate and require more memory.

Improvements in imaging technology may result in the detection of cancerous tumors at early stages in the tumor development. As such, the size of the tumor may be small (e.g., less than 5-10 mm), necessitating accurate and targeted radiation at that tumor to minimize damage to healthy tissue. Without accurate dose predictions, it is difficult to create an optimal treatment plan for the patient (e.g., minimizing damage to healthy tissue while shrinking the size of the cancerous tumor), verify the treatment plan (e.g., calculate final dose calculations), and validate the treatment plan.

In the context of such small tumors, empirical models are underperforming, due, in part, to the generality of such models. For example, empirical models, such as the analytical anisotropic algorithm (AAA), model the source by modeling contributions of primary radiation and secondary radiation to the model. Primary radiation may be described as the radiation originating from the source of the accelerator without touching any of the walls of the accelerator. Secondary radiation (including secondary photons and electrons) may be described as the radiation that results from a scattering of the photons and electrons from within the accelerator and arriving at the patient. Conventionally, secondary radiation measurements have been determined using measurements of radiation in water.

Generally precomputed quantities (such as those used to model radiation behavior in dose spread kernel algorithms) and generalized assumptions should be avoided when calculating dosages received by patients.

SUMMARY

For the aforementioned reasons, there is a desire for a model that can quickly and accurately calculate a dose deposition. Disclosed herein is an artificial intelligence model configured to boost the accuracy of calculated dose distributions (or dose depositions). The model may receive a calculated dose distribution and improve the calculated dose distribution by inferring relationships between dosing algorithms. Specifically, the model may remove artificial artifacts associated with particular dosing algorithms. Removing one or more artificial artifacts and mapping the results of a first dosing algorithm to those results comparable to a second dosing algorithm may improve the usage of computational resources. Instead of consuming significant power, resources, and time performing an accurate dosing algorithm characterized by long run-times, the model described herein may mimic the results of the dosing algorithm without performing the dosing algorithm. For example, the model may be configured to produce a dosage calculation that is as accurate as a dosage calculation determined using MC simulations without having to perform the MC simulation. Accordingly, the system described herein does not expend all of the resources that a similar system would have expended to perform a MC simulation to determine the dosage deposition.

In one embodiment, a method may comprise receiving, by the processor, a medical image; determining, by the processor, a dose deposition using the medical image and determined by a first dose deposition model indicating a minimum dose deposition; and determining, by the processor, a dose deposition for the medical image by executing an artificial intelligence model using the medical image and the dose deposition determined by the first dose deposition model, wherein the artificial intelligence model is trained to simulate a dose deposition determined by a second dose deposition model using a set of training medical images, each training medical image having a corresponding first training dose deposition determined by the first dose deposition model and a second training dose deposition determined by the second dose deposition model.

The first dose deposition model may represent an initial dose deposition, and the second dose deposition model may adjust the initial dose deposition. In a configuration, the first dose deposition model may determine a flux distribution abstracting a dose reaction rate with the anatomical region of the patient to determine a dose distribution. In a configuration, the second dose deposition model may employ a nondeterministic particle behavior simulator (e.g., using Monte Carlo simulation) and/or direct dose measurements to determine a dose distribution. The minimum dose deposition determined using the first dose deposition model may be adjusted using the artificial intelligence model, which is trained using the second dose deposition model.

The artificial intelligence model may be a neural network.

The set of training medical images and corresponding first training dose deposition determined by the first dose deposition model and the second training dose deposition determined by the second dose deposition model may correspond to a particular anatomical region.

The set of training medical images and corresponding first training dose deposition determined by the first dose deposition model and the second training dose deposition determined by the second dose deposition model may correspond to a particular clinic.

The set of training medical images and corresponding first training dose deposition determined by the first dose deposition model and the second training dose deposition determined by the second dose deposition model may correspond to a particular radiotherapy machine.

The second training dose deposition may be modified according to a preference of a medical professional, the artificial intelligence model being trained to simulate the dose deposition determined by the second dose deposition model and modified according to the preference of the medical professional.

In another embodiment, a system may comprise a server comprising a processor and a non-transitory computer-readable medium containing instructions that when executed by the processor cause the processor to perform operations comprising: receiving a medical image; determining a dose deposition using the medical image, and determined by a first dose deposition model indicating a minimum dose deposition; determining a dose deposition for the medical image by executing an artificial intelligence model using the medical image and the dose deposition determined by the first dose deposition model, wherein the artificial intelligence model is trained to simulate a dose deposition determined by a second dose deposition model using a set of training medical images, each training medical image having a corresponding first training dose deposition determined by the first dose deposition model and a second training dose deposition determined by the second dose deposition model.

The first dose deposition model may represent an initial dose deposition, and the second dose deposition model may adjust the initial dose deposition.

The first dose deposition model may determine a flux distribution abstracting a dose reaction rate with the anatomical region of the patient.

The second dose deposition model may employ a nondeterministic particle behavior simulator and/or direct dose measurements.

The minimum dose deposition may be determined using the first dose deposition model is adjusted using the artificial intelligence model.

The artificial intelligence model may be a neural network.

The set of training medical images and corresponding first training dose deposition determined by the first dose deposition model and the second training dose deposition determined by the second dose deposition model may correspond to a particular anatomical region.

The set of training medical images and corresponding first training dose deposition determined by the first dose deposition model and the second training dose deposition determined by the second dose deposition model may correspond to a particular clinician.

The set of training medical images and corresponding first training dose deposition determined by the first dose deposition model and the second training dose deposition determined by the second dose deposition model may correspond to a particular radiotherapy machine.

The second training dose deposition may be modified according to a preference of a medical professional, the artificial intelligence model being trained to simulate the dose deposition determined by the second dose deposition model and modified according to the preference of the medical professional.

BRIEF DESCRIPTION OF THE DRAWINGS

Non-limiting embodiments of the present disclosure are described by way of example with reference to the accompanying figures, which are schematic and are not intended to be drawn to scale. Unless indicated as representing the background art, the figures represent aspects of the disclosure.

DETAILED DESCRIPTION

Figure 1:
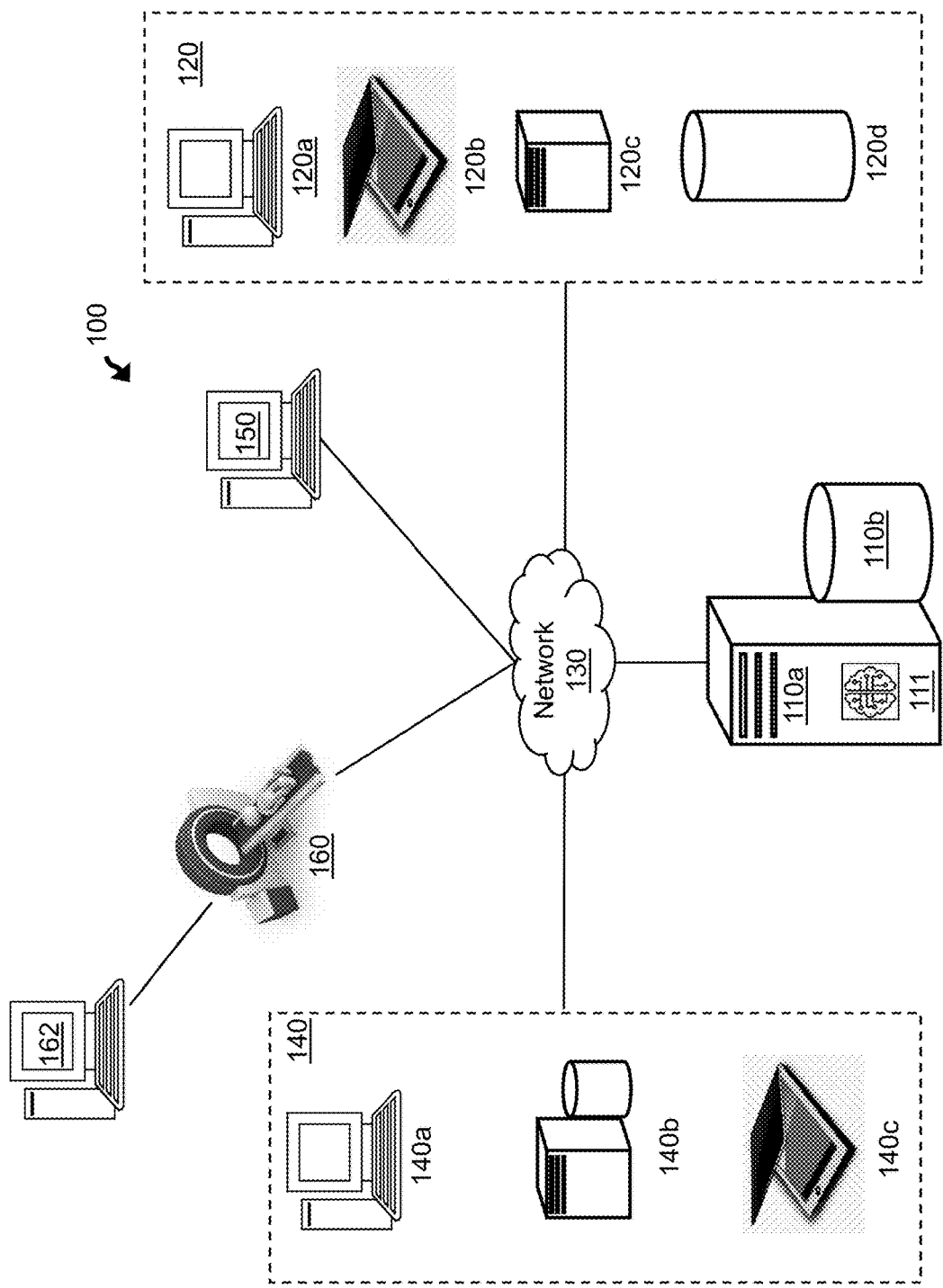
FIG. 1 illustrates components of a dose boosting system, according to an embodiment.

Reference will now be made to the illustrative embodiments depicted in the drawings, and specific language will be used here to describe the same. It will nevertheless be understood that no limitation of the scope of the claims or this disclosure is thereby intended. Alterations and further modifications of the inventive features illustrated herein, and additional applications of the principles of the subject matter illustrated herein, which would occur to one skilled in the relevant art and having possession of this disclosure, are to be considered within the scope of the subject matter disclosed herein. Other embodiments may be used and/or other changes may be made without departing from the spirit or scope of the present disclosure. The illustrative embodiments described in the detailed description are not meant to be limiting of the subject matter presented.

Clinics may utilize software solutions for radiation therapy treatment planning. The software solutions may analyze patient data, clinical guidelines, clinical goals, and a multitude of other factors to generate a customized treatment plan for a patient including an optimal dose deposition that maximizes radiation that targets the cancerous tumor and minimizes radiation affecting healthy tissue. The software solutions may include a set of computer-readable instructions stored on a non-transitory computer medium and configured to be executed by a processor to carry out this functionality.

FIG. 1 illustrates components of a dose boosting system 100, according to an embodiment. The system 100 may include an analytics server 110a, system database 110b, machine learning models 111, electronic data sources 120a-d (collectively electronic data sources 120), end-user devices 140a-c (collectively end-user devices 140), an administrator computing device 150, and a medical device 160 having a medical device computer 162. Various components depicted in FIG. 1 may belong to a radiotherapy clinic at which patients may receive radiotherapy treatment, in some cases via one or more radiotherapy machines located within the clinic (e.g., medical device 160). The above-mentioned components may be connected to each other through a network 130. Examples of the network 130 may include, but are not limited to, private or public LAN, WLAN, MAN, WAN, and the Internet. The network 130 may include wired and/or wireless communications according to one or more standards and/or via one or more transport mediums.

The communication over the network 130 may be performed in accordance with various communication protocols such as Transmission Control Protocol and Internet Protocol (TCP/IP), User Datagram Protocol (UDP), and IEEE communication protocols. In one example, the network 130 may include wireless communications according to Bluetooth specification sets or another standard or proprietary wireless communication protocol. In another example, the network 130 may also include communications over a cellular network, including, e.g., a GSM (Global System for Mobile Communications), CDMA (Code Division Multiple Access), EDGE (Enhanced Data for Global Evolution) network.

The system 100 is not confined to the components described herein and may include additional or other components, not shown for brevity, which are to be considered within the scope of the embodiments described herein.

The analytics server 110a may execute an electronic platform configured to use various computer models 111 (including artificial intelligence and/or machine learning models) to display RTTP information including a boosted dose deposition. The electronic platform may include one or more graphical user interfaces (GUIs) displayed on each electronic data source 120, end-user devices 140, administrator computing device 150, and/or medical computing devices 162. An example of the electronic platform generated and hosted by the analytics server 110a may be a web-based application or a website configured to be displayed on different electronic devices, such as mobile devices, tablets, personal computers, and the like. In a non-limiting example, a physician operating the physician device 120b may access the platform, input patient attributes and other data (such as medical images), and further instruct the analytics server 110a to boost a calculated dose deposition using one or more machine learning models 111.

The operations invoked by the analytics server 110a to determine a boosted dose deposition may be part of the operations in a sequence of operations to optimize a patient treatment plan. That is, the results of the machine learning model 111 may be transmitted to other processors or devices to optimize other radiotherapy treatment attributes.

A medical professional may use the medical professional device (e.g., medical professional device 140c) as both a device to display results predicted by the analytics server 110a and in some cases as an electronic data source (e.g., electronic data source 120b) to train the machine learning models 111.

The analytics server 110a may host a website accessible to users operating any of the electronic devices described herein (e.g., end-users, medical professionals), where the content presented via the various webpages may be controlled based upon each particular user's role or viewing permissions. The analytics server 110a may be any computing device comprising a processor and non-transitory machine-readable storage capable of executing the various tasks and processes described herein. The analytics server 110a may employ various processors such as central processing units (CPU) and graphics processing unit (GPU), among others. Non-limiting examples of such computing devices may include workstation computers, laptop computers, server computers, and the like. While the system 100 includes a single analytics server 110a, the analytics server 110a may include any number of computing devices operating in a distributed computing environment, such as a cloud environment.

The analytics server 110a may execute software applications configured to display the electronic platform (e.g., host a website), which may generate and serve various webpages to each electronic data source 120 and/or end-user devices 140. Different users may use the website to view and/or interact with the boosted dose calculations. Servers, such as analytics server 110a, server 120c and/or clinic server 140b, may use the boosted dose deposition in downstream processing (e.g., optimize one or more other radiation parameters and/or treatment directives). The analytics server 110a may also store data associated with each user operating one or more electronic data sources 120 and/or end-user devices 140.

The analytics server 110a may be configured to require user authentication based upon a set of user authorization credentials (e.g., username, password, biometrics, cryptographic certificate, and the like). The analytics server 110a may access the system database 110b configured to store user credentials, which the analytics server 110a may be configured to reference in order to determine whether a set of entered credentials (purportedly authenticating the user) match an appropriate set of credentials that identify and authenticate the user.

The analytics server 110a may generate and host webpages based upon a particular user's role within the system 100. In such implementations, the user's role may be defined by data fields and input fields in user records stored in the system database of the clinic server 110b. The analytics server 110a may authenticate the user and may identify the user's role by executing an access directory protocol (e.g., LDAP). The analytics server 110a may generate webpage content that is customized according to the user's role defined by the user record in the system database 110b.

The analytics server 110a may receive patient data (e.g., medical images, height, weight, diagnosis, age, equipment, etc.) from a user or retrieve such data from a data repository, analyze the data, and display the results on the electronic platform. The analytics server 110a may also preprocess the patient data (e.g., automatically segment the medical image). In a non-limiting example, the analytics server 110a may query and retrieve RTTP data (including medical images and other patient data) from the database 120d and execute one or more instructions to model a source of radiation and determine a dose deposition for the patient. The analytics server 110a may then display the results to be interacted with via the electronic platform on the administrator computing device 150, the end-user devices 140, medical computing device 162, and/or the electronic physician device 120b. The analytics server 110a may display boosted dose depositions for proton radiation, photon radiation, and electron radiation.

The analytics server 110a may also use the calculated dose depositions in one or more downstream applications. For example, a downstream application may determine information such as radiation parameters including beam angles, side effect prediction, machine therapy attributes such as gantry position, beam blocking devices, treatment frequency, treatment timing, and treatment modalities, among others. Further, the analytics server 110a may transmit the calculated dose depositions to one or more other servers (e.g., clinic server 140b) such that a different device uses the dose deposition in one or more downstream applications. Additionally, or alternatively, the analytics server 110a (or other server) may adjust the configuration of one of the end-user devices 140 (e.g., the end-user device 140c) based on the determined dosages.

The analytics server 110a may be configured to execute various dosing algorithms. For example, some dosage calculation methods executed by the analytics server 110a include deterministic methods, such as Acuros® or Acuros® XB dosing algorithm. The dosing algorithm computes the dose deposited to the patient by solving the Linear Boltzmann Transport Equation (LBTE). The LBTE governs how particles stream through a medium, how particles scatter within the medium, and how particles are absorbed with the medium. Deterministic methods (such as Acuros®/Acuros® XB dosing algorithms) discretize the LBTE into a matrix and iteratively invert the matrix. The solution is a flux distribution (or fluence) that abstracts the dose reaction rate with the medium. The flux is then mapped from the flux to the dose imparted to the medium, and the dose imparted to a water equivalent medium (e.g., dose to material vs dose to medium). Errors commonly associated with using deterministic methods to solve the LBTE are systematic errors that result from discretizing variables in angle, energy, and/or space. In some embodiments, the analytics server 110a may be configured to improve the convergence speed of deterministic methods (e.g., decrease the run-time) by increasing the step-sizes in the discretization process. However, increasing the step-size results in decreased accuracy.

The analytics server 110a is also configured to execute nondeterministic methods such as MC simulations as a mechanism for solving the LBTE. MC simulations solve LBTE in open form, and the errors associated with MC simulations are associated with the randomness of simulating each particle as the particle interacts with a medium.

The analytics server 110a is configured to boost dose deposition results from a first dosing algorithm (such as determined using deterministic methods) to mimic (replicate, or simulate) the dose deposition results from a different dosing algorithm (such as MC) using machine learning models 111. As such, the dose deposition executed via the first dosing algorithm is an initial dose deposition (or a minimum dose deposition) that is improved.

The analytics server 110a executes various machine learning models 111 (stored within the system database of the clinic server 140b or the analytics server 110b) to boost the dose depositions determined by a first dosing algorithm to mimic dose depositions determined by a second dosing algorithm. The analytics server 110a may then display the results to be interacted with via the electronic platform on the administrator computing device 150, the medical professional device 120b, medical computing device 162, and/or the end-user devices 140.

The electronic data sources 120 may represent various electronic data sources that contain, retrieve, and/or input data associated with a patient's treatment plan including patient data and treatment data. For instance, the analytics server 110a may use the clinic computer 120a, medical professional device 120b, server 120c (associated with a physician and/or clinic), and database 120d (associated with the physician and/or the clinic) to retrieve/receive data associated with the patient's treatment plan.

End-user devices 140 may be any computing device comprising a processor and a non-transitory machine-readable storage medium capable of performing the various tasks and processes described herein. Non-limiting examples of an end-user device 140 may be a workstation computer, laptop computer, tablet computer, and server computer. In operation, various users may use end-user devices 140 to access the GUI operationally managed by the analytics server 110a. Specifically, the end-user devices 140 may include clinic computer 140a, clinic server 140b, and a medical device professional 140c. Even though referred to herein as "end-user" devices, these devices may not always be operated by end-users. For instance, the clinic server 140b may not be directly used by an end-user. However, the results stored onto the clinic server 140b may be used to populate various GUIs accessed by an end-user via the medical professional device 140c.

The administrator computing device 150 may represent a computing device operated by a system administrator. The administrator computing device 150, along with the medical professional device 140c, medical professional device 120b, medical computing device 162, and the like, may be configured to display RTTP information such dose depositions determined by the analytics server 110a; display various analytic metrics determined during training of one or more machine learning models and/or systems; monitor various machine learning models 111 utilized by the analytics server 110a, electronic data sources 120, and/or end-user devices 140; review feedback; and/or facilitate training or retraining (calibration) of the machine learning models 111 that are maintained by the analytics server 110a.

The medical device 160 may be a radiotherapy machine (e.g., a linear accelerator, particle accelerator (including circular accelerators), or a cobalt machine)) configured to implement a patient's radiotherapy treatment. The medical device 160 may also include an imaging device capable of emitting radiation such that the medical device 160 may perform imaging according to various methods to accurately image the internal structure of a patient. For instance, the medical device 160 may include a rotating system (e.g., a static or rotating multi-view system). A non-limiting example of a multi-view system may include a stereo systems (e.g., two systems may be arranged orthogonally). The medical device 160 may also be in communication with a medical computing device 162 that is configured to display various GUIs discussed herein. For instance, the analytics server 110a may display the results predicted by the machine learning model 111 onto the medical computing device 162.

In operation, a medical professional may access an application executing on the medical professional device 120b and input RTTP data (e.g., patient information, patient diagnosis, radiation therapy radiation requirements, and thresholds). The analytics server 110a then uses a patient identifier to query patient data (e.g., patient anatomy and/or medical images) from the electronic data sources 120. The analytics server 110*a* may also use a radiotherapy machine identifier to query data from the electronic data sources 120 associated with radiotherapy machines (e.g., physical characteristics, dimensions, radiation output). In some embodiments, the analytics server 110*a* is configured to retrieve a machine learning model 111 based on patient data (e.g., a particular machine learning model trained to boost dose depositions associated with a specific anatomical region of a patient such as the lung, abdomen, heart, etc. The analytics server 110*a* may also identify a clinic associated with the patient (e.g., clinic performing the treatment) and retrieve one or more files associated with treatment templates, radiotherapy machine, and clinic rules. The analytics server 110*a* may then utilize the systems and methods described herein to determine a boosted dose distribution from the patient data and the medical device 160 and display the results onto the physician device 120*b*, the clinic computer 140*a*, and/or the medical computing device 162.

The analytics server 110*a* may be in communication (real-time or near real-time) with the medical computing device 162, end-user device 140 and/or electronic data sources 120, such that a server/computer hosting the medical device 160 can adjust the medical device 160 based on the calculated dose deposition. For instance, the radiotherapy machine may adjust the gantry, beam blocking device (e.g., MLC), and couch based on the dosage calculations. The analytics server 110*a* may transmit instructions to the radiotherapy machines indicating any number or type of radiation parameters, beam angles, and/or treatment directives to facilitate such adjustments.

Machine learning models 111 (e.g., neural networks, random forest, support vector machines, or other deep learning models), trained to boost dose calculation results from a first dosing algorithm to a second dosing algorithm may be stored in the system database 110*b* and/or analytics server 110*a*. Although exemplified using neural networks, it should be understood that any alternative and/or additional supervised learning model(s) may be used to implement the machine learning models 111.

Figure 2:
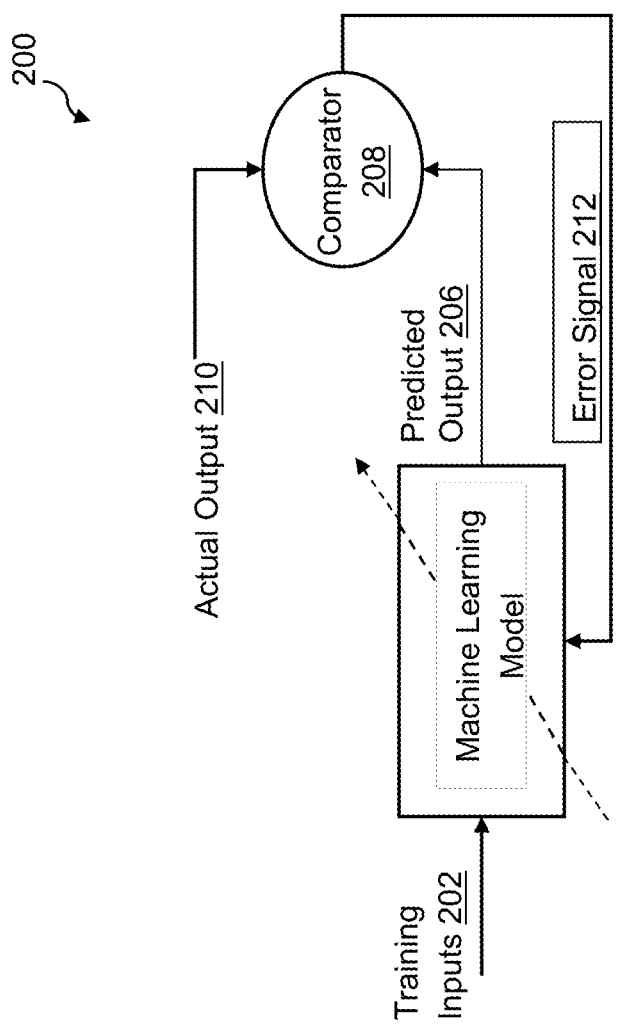
FIG. 2 illustrates a system using supervised learning that may be used to infer relationships between dose depositions determined using different dosing algorithms, according to an embodiment.

FIG. 2 illustrates a system 200 using supervised learning that may be used to infer relationships between dose depositions determined using different dosing algorithms, according to an embodiment. In some embodiments, the machine learning model may be trained to infer relationships between dose depositions determining according to a first dosing algorithm and direct dose measurements. The direct dose deposition may be the measured dose imparted to the patient.

Training a machine learning model to boost a minimum dose deposition determined by a first dosing algorithm to an improved dose deposition determined by a second dosing algorithm may boost the accuracy of the dose deposition results, reduce computational resources that would have been necessary to calculate the dose deposition results determined by the second dosing algorithm, and reduce the run-time necessary to determine dose deposition results determined by the second dosing algorithm by mimicking the results determined by the second dosing algorithm without executing the second dosing algorithm.

Supervised learning is a method of training a machine learning model given input-output pairs. An input-output pair is an input with an associated known output (e.g., an expected output, a labeled output). For ease of description, the supervised learning system is trained to determine a relationship between dose depositions determined using deterministic methods and MC, but it should be appreciated that the supervised system may be trained to determine a relationship between other dosing algorithms. For example, it may be advantageous to boost dose depositions determined via Kernel methods to mimic dose depositions determined via MC simulations. Using the supervised system to learn the relationship between Kernel methods and MC simulations is beneficial because Kernel methods generally have short run-times but inaccurate solutions.

The machine learning model 200 may be trained during a training phase on known input-output pairs (e.g., medical images with dose depositions determined using deterministic methods and corresponding dose depositions determined using MC) such that the machine learning model 200 learns how to predict known outputs given known inputs. Once the machine learning model 200 has learned how to predict known input-output pairs, the machine learning model 200 can operate on unknown inputs to predict an output.

To train the machine learning model 200 using supervised learning, training inputs 202 and actual outputs 210 may be provided to the machine learning model 200. In some embodiments, training inputs 202 may include historic medical images (computed tomography (CT) images, cone beam CT images (CBCT), four-dimensional CT images (e.g., CT images over time), magnetic resonance imaging (MM) images, positron emission tomography (PET) images, ultrasound images, images obtained via some other imaging modality, or a combination thereof) and a dose deposition determined using deterministic methods. Actual outputs 210 may include a dose deposition determined using MC simulations using the same historic medical images. The training inputs 202 and actual outputs 210 may be stored in memory or other data structure accessible by the machine learning model 200.

The analytics server may train machine learning model 200 according to various levels of granularity. For example, the analytics server may train the machine learning model 200 to boost dose calculations on specific anatomical regions of a patient. For instance, the training inputs 202 may be medical images of a particular part of a patient (e.g., a lung) and the corresponding dose depositions determined via deterministic methods. Accordingly, the actual outputs 210 will be the corresponding dose depositions determined using MC simulations and the same medical image of the particular part of the patient. The analytics server may also train the machine learning model 200 to boost dose calculations according to radiotherapy machines. For example, the training inputs 202 may be the medical images captured using a particular radiotherapy machine and the corresponding dose depositions determined via deterministic methods. The actual outputs 210 will be the corresponding dose depositions determined using MC simulations and the same radiotherapy machine. Additionally or alternatively, the analytics server may train the machine learning model 200 using medical images captured from a particular clinic and dose depositions determined by deterministic methods/MC simulations. That is, the training inputs 202 may be the medical images captured at a particular clinic and the corresponding dose depositions determined via deterministic methods. The actual outputs 210 will be the corresponding dose depositions determined using MC simulations and the same medical image captured at the particular clinic. Generally, the analytics server may train the machine learning model 200 to boost any dose dosing algorithm that suffers from artificial artifacts. For example, common artifacts associated with CBCT imaging may be removed such that the accuracy of the dose deposition improves.

In some embodiments, one or more medical professionals may adjust the dose depositions determined by deterministic methods and/or MC simulations. For example, given a dose deposition determined using a particular dosing algorithm, a medical professional may use a "safer" dose deposition for treatment as compared to the dose deposition determined using the dosing algorithm. Each medical professional may have a different subjective understanding of "safe" dosage distributions, resulting in a unique preference for each medical professional. The analytics server may store the modifications to the dose depositions for each medical professional. By training a machine learning model 200 only on dose depositions modified by a particular medical professional, the machine learning model 200 will learn the preferences of the medical professional. For example, the training inputs 202 may be medical images and corresponding dose depositions determined via deterministic methods. The actual outputs 210 will be the dose deposition determined using MC simulations and the same medical images, modified by one or more preferences of the medical professional. In some implementations, the machine learning model 200 may be trained to learn the preferences of medical professionals according to particular anatomical regions of a patient. For example, a medical professional may prefer to radiate one anatomical region of a patient more than another anatomical region of a patient. In this manner, the analytics server trains the machine learning model 200 according to the preferences of medical professionals.

As described herein, the analytics server may also train the machine learning model 200 using other dose calculation methods. For example, the analytics server may train the machine learning model 200 using medical images and dose depositions determined via Kernel methods (as training inputs 202) and dose depositions determined via MC simulations (as actual outputs 210).

The machine learning model 200 may use the training inputs 202 (e.g., images and dose depositions determined via deterministic methods) to predict outputs 206 (e.g., a predicted dose calculation mimicking a MC simulation), by applying the current state of the machine learning model 200 to the training inputs 202. The comparator 208 compares the predicted outputs 206 to the actual outputs 210 (e.g., the actual dose calculation determined using MC simulations) to determine an amount of error or differences.

During training, the error (represented by error signal 212) determined by the comparator 208 may be used to adjust the weights in the machine learning model 200 such that the machine learning model 200 changes (or learns) over time to mimic the dose deposition determined using MC simulations using only the initial dose calculation determined using deterministic methods. The analytics server may train the machine learning model 200 using the backpropagation algorithm, for instance. The backpropagation algorithm operates by propagating the error signal 212. The analytics server may calculate the error signal 212 each iteration (e.g., each pair of training inputs 202 and associated actual outputs 210), batch, and/or epoch and propagated through all of the algorithmic weights in the machine learning model 200 such that the algorithmic weights adapt based on the amount of error. The error is minimized using a loss function. Non-limiting examples of loss functions may include the square error function, the root mean square error function, and/or the cross-entropy error function.

The weighting coefficients of the machine learning model are tuned to reduce the amount of error thereby minimizing the differences between (or otherwise converging) the predicted output 206 and the actual output 210. For instance, because the machine learning model is being trained to mimic MC dose distributions, the mimicked MC dose distribution will iteratively converge to the dose distribution calculated by executing a MC simulation. The analytics server trains the machine learning model 200 until the error determined at the comparator 208 is within a certain threshold (or a threshold number of batches, epochs, or iterations have been reached). The trained machine learning model and associated weighting coefficients may subsequently be stored in memory or other data repository (e.g., a database) such that the trained machine learning model may be employed on unknown data (e.g., not training inputs 202). Once trained and validated, the machine learning model 200 may be employed during testing (or inference). During testing, the machine learning model ingests unknown data (e.g., medical images and corresponding dose deposition determined using deterministic methods) to predict a dose deposition that would be similar to the calculated dose deposition determined by executing a MC simulation.

Figure 3:
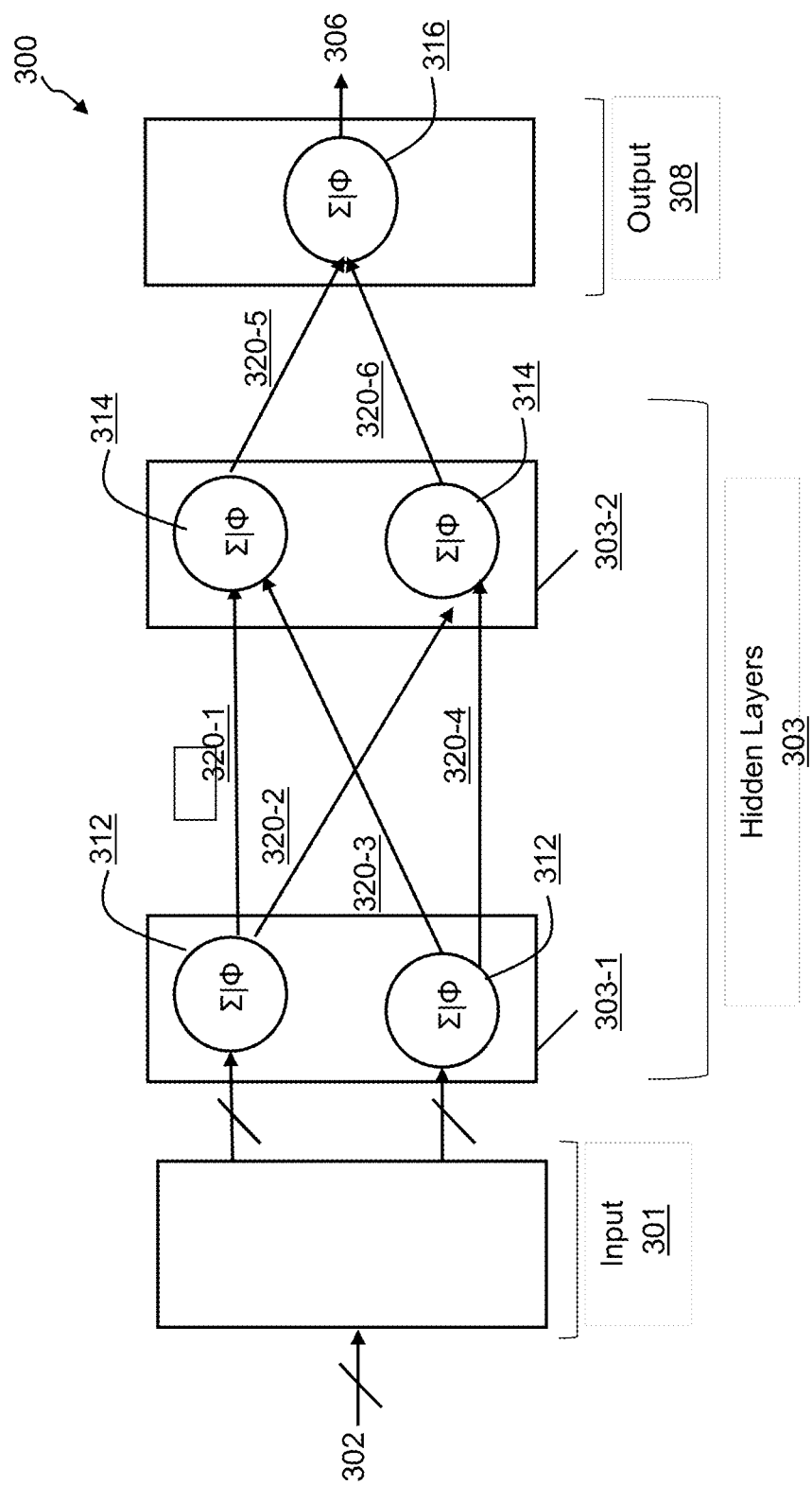
FIG. 3 illustrates a block diagram of a simplified neural network model, according to an embodiment.

FIG. 3 illustrates a block diagram of a simplified neural network model 300 is shown, according to an example embodiment. The neural network is an example of the machine learning model (e.g., machine learning model 200 of FIG. 2) that is trained to boost dose depositions. The neural network model 300 may be a convolutional neural network (CNN), graph neural network, Fourier neural network, physics informed neural network, and the like. If the neural network model 300 is a CNN, the CNN may contain additional layers (not shown) that each perform a specific operation (e.g., convolution, pooling, etc.). Convolutional layers may act as feature extractors by convolving filters (or kernels) with an input image. The output of the convolutional layers may be a feature map that highlights the effect of applying the specific filter on the input. Pooling layers may be layers that reduce the dimensionality of feature maps. If the neural network model 300 is a graph neural network, the analytics server may convert a medical image received by the neural network model 300 to a graph representing objects (nodes) and relationships (edges) in the medical image to learn relationships based on the nodes, the edges, and/or the graph. If the neural network model 300 is a Fourier neural network, the activation function in each node 314 may be sinusoidal (as opposed to sigmoid functions, hyperbolic functions, and/or rectified linear activation functions) to better approximate periodic functions. Approximating periodic functions allows the neural network model 300 to predict periodic solutions for relationships described by partial differential equations. Similarly, if the neural network model 300 is a physics informed neural network, the neural network may be trained to learn relationships described by laws of physics represented using partial differential equations. The neural network model 300 may include a stack of distinct layers (vertically oriented) that transform a variable number of inputs 302 being ingested by an input layer 304, into an output 306 at the output layer 308.

The neural network model 300 may include a number of hidden layers 303 (or fully connected layers) between the input layer 304 and output layer 308. The hidden layers 303 are fully connected layers because each node 312 in the hidden layer 303-1 is connected to each node 314 in the hidden layer 303-2. In the neural network model 300, the first hidden layer 303-1 has nodes 312, and the second hidden layer 303-2 has nodes 314. The nodes 312 and 314 perform a particular computation and are interconnected to the nodes of adjacent layers. Each of the nodes 312, 314, 316 sum up the values from adjacent nodes and apply an activation function, allowing the neural network model 300 to detect nonlinear patterns in the inputs 302. The detection of the nonlinear patterns allows the neural network to infer gaps in the inputs 302 that result in the outputs 306. Each of the nodes 312, 314 316 are interconnected by weights 320-1, 320-2, 320-3, 320-4, 320-5, 320-6 (collectively referred to as weights 320). Weights 320 are tuned during training to adjust the strength of the node. The adjustment of the strength of the node facilitates the neural network's ability to predict an accurate output 306 (e.g., the neural network model 300 ability to learn nonlinear relationships).

In some embodiments, the output 306 may be one or more numbers (e.g., a multidimensional matrix of real numbers). The one or more numbers or matrix of real numbers may represent dose depositions in each voxel.

A medical professional at a radiotherapy clinic may access an end-user device 140 located at the clinic or access an account associated with the clinic. The medical professional may provide an input at a user interface that causes the end-user device 140 to transmit a request to access a machine learning model 111 that is associated with the clinic and/or the radiotherapy machines located within the clinic. The request may include an identifier associated with the machine learning model 111, the clinic, the medical professional, an anatomical region of a patient, and/or the set of radiotherapy machines that the analytics server 110*a* may use as a key in a look-up table to identify the machine learning model 111. The analytics server 110*a* may receive the request and, in some cases, after authenticating the user, identify the machine learning model 111 via the identifier. The analytics server 110*a* may transmit the identified machine learning model 111 to the end-user device 140 or send an alert indicating the end-user device is authorized to access the model(s) 111. Upon receipt or access to the machine learning model 111, the end-user device 140 may perform the systems and methods described herein to train or retrain the machine learning model 111 to mimic dose calculations of dose calculation methods.

Figure 4:
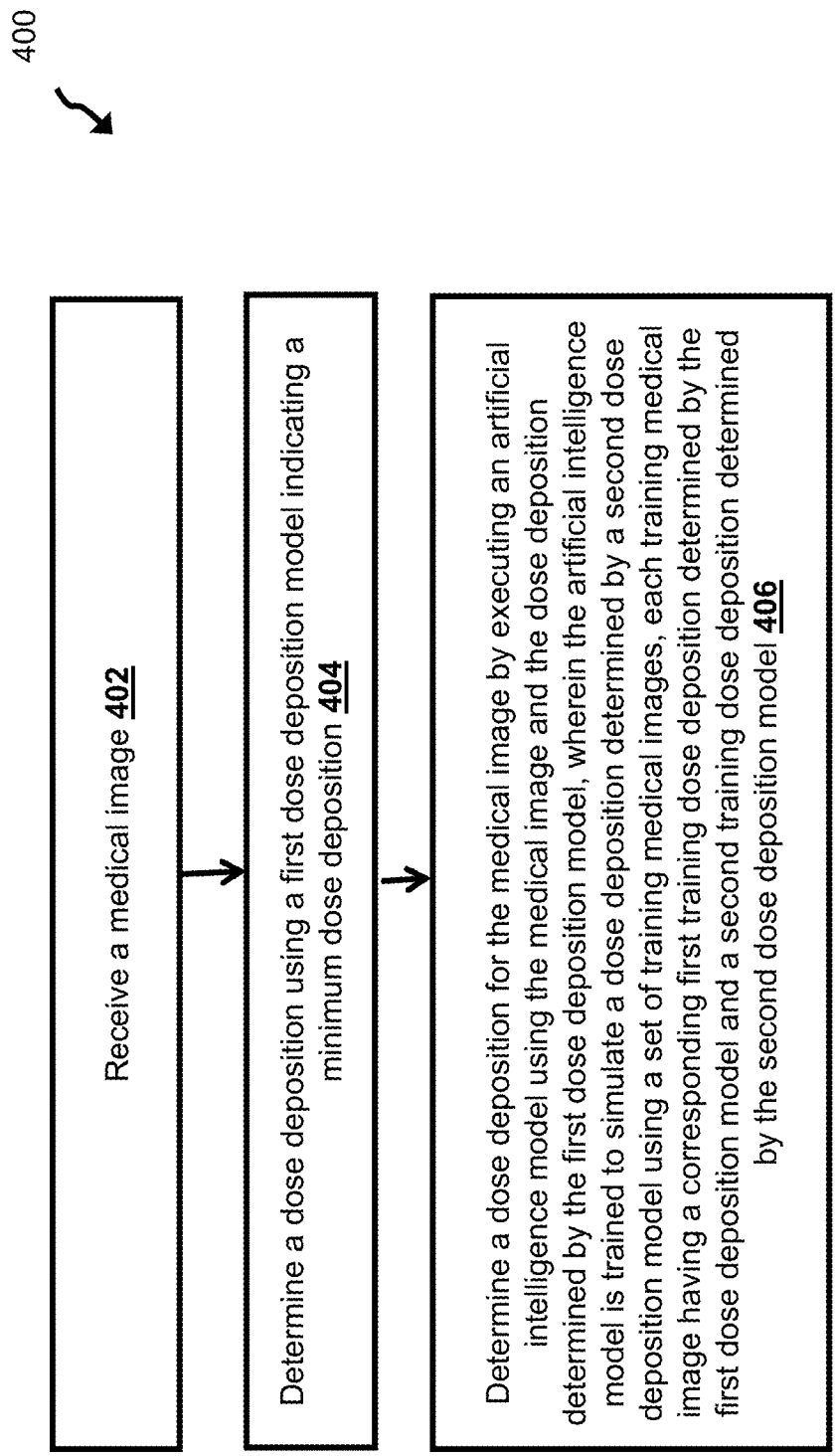
FIG. 4 illustrates a flow diagram of a dose boosting system, according to an embodiment.

FIG. 4 illustrates a flow diagram of a dose boosting system, according to an embodiment. The method 400 includes steps for boosting a dose deposition4, according to an embodiment. The method 400 may include steps 402-406. However, other embodiments may include additional or alternative steps, or may omit one or more steps altogether.

The method 400 is described as being executed by an analytics server, such as the analytics server described in FIG. 1. The analytics server may employ one or more CPUs and GPUs to perform one or more steps of method 400. The CPUs and/or GPUs may be performed in part by the analytics server and in part by one or more other servers and/or computing devices. The servers and/or computing devices employing the CPUs and GPUs may be local and/or remote (or some combination). For example, one or more virtual machines in a cloud may employ one or more CPUs and GPUs to perform one or more steps of method 400. A hybrid CPU and GPU implementation may improve the speed associated with training a machine learning model to boost dose calculations. However, one or more steps of method 400 may be executed by any number of computing devices operating in the distributed computing system described in FIG. 1. For instance, one or more computing devices may locally perform part or all of the steps described in FIG. 4.

In step 402, the analytics server receives a medical image of a particular anatomical region of a patient. The medical image may be a medical image captured by a radiotherapy machine and/or other machine configured to image an anatomical region of a patient (e.g., CT images, CBCT images, 4D CT images, MRI images, PET images, ultrasound images, and/or images obtained via some other modality). The medical image may also be a medical image retrieved from a database (e.g., database 120*d*, database 110*b*, external databases, etc.).

In step 404, the analytics server determines a dose deposition using a first dose deposition model indicating a minimum dose deposition. The analytics server may feed the received images directly into the first dose deposition model. Additionally or alternatively, the analytics server may transform the received medical image before feeding the medical image into the first dose deposition model. For example, the analytics server may normalize the medical image, scale the medical image, transform the medical image from a first dimension to a second dimension (e.g., transform a 3D medical image into a 2D medical image by forward projecting the 3D voxels into 2D pixels, transform a 2D medical image into a 3D medical image using the Feldkamp-Davis-Kress (FDK) algorithm), etc.

The first dose deposition model may be a dosing algorithm characterized by a short-run time, for example. The advantage of executing a dosing algorithm characterized by a short run-time is that unnecessary resources are not expended multiple times. The dose deposition determined by the first dose deposition model is not the final dose deposition. The dose deposition determined by the first dose deposition model is the initial dose deposition (or minimum dose deposition) that is boosted by an artificial intelligence model, as discussed with respect to the step 406. Accordingly, minimizing the resources expended to compute the first dose deposition is beneficial such that resources are not unnecessarily expended multiple times (e.g., time, computational resource consumption, processing power, etc.) In some embodiments, the first dose deposition model may determine the dose deposition using deterministic methods.

In step 406, the analytics server determines a dose deposition for the medical image by executing an artificial intelligence model using the medical image and the dose deposition determined by the first dose deposition model. As described herein, the artificial intelligence model is trained to simulate a dose deposition determined by a second dose deposition model. The second dose deposition model may be characterized as a high-accuracy dosing algorithm. For example, the second dose deposition model may be a MC simulation.

During training, the artificial intelligence model receives medical images, dose depositions determined by the first dose deposition model, and corresponding dose depositions determined by the second dose deposition model. The analytics server iteratively trains the artificial intelligence model to infer relationships between the first dose deposition model and the second dose deposition model. Accordingly, the artificial intelligence model learns to receive a minimum dose deposition determined by the first dose deposition model and boost the minimum dose deposition (e.g., the accuracy of the dose deposition) to simulate the results/accuracy of a dose deposition determined by the second dose deposition model. In this manner, the accuracy of the results of a dose deposition determined by the second dose deposition model are simulated without having to execute the second dose deposition model.

The artificial intelligence model may be trained in narrow/granular applications. For example, the artificial intelligence model may be trained to boost dose depositions of particular anatomical regions of the patient using medical images of the particular anatomical regions of the patient. The artificial intelligence model may also be trained to boost dose depositions of particular radiotherapy machines, boost dose depositions of particular clinics, and boost dose depositions according to medical professional preferences, and the like. The boosted dose depositions result in a boosted dose reaction rate simulating dose depositions determined using nondeterministic methods.

In a non-limiting example, a processor trains an artificial intelligence model to increase the accuracy of dose deposition calculations. The artificial intelligence model is trained using a set of training medical images and corresponding dose deposition calculations determined using deterministic methods and non-deterministic methods. The artificial intelligence model learns to predict the dose deposition calculations determined using non-deterministic methods using dose deposition calculations determined using deterministic methods and the medical image. As such, the artificial intelligence model improves the accuracy of the dose deposition calculations determined using deterministic methods. The trained artificial intelligence model is applied to medical images and dose deposition calculations determined using deterministic methods to simulate the dose deposition calculation determined using non-deterministic methods.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of this disclosure or the claims.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting of the claimed features or this disclosure. Thus, the operation and behavior of the systems and methods were described without reference to the specific software code being understood that software and control hardware can be designed to implement the systems and methods based on the description herein.

When implemented in software, the functions may be stored as one or more instructions or code on a non-transitory computer-readable or processor-readable storage medium. The steps of a method or algorithm disclosed herein may be embodied in a processor-executable software module, which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used herein, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the embodiments described herein and variations thereof. Various modifications to these embodiments will be readily apparent to those skilled in the art, and the principles defined herein may be applied to other embodiments without departing from the spirit or scope of the subject matter disclosed herein. Thus, the present disclosure is not intended to be limited to the embodiments shown herein but is to be accorded the widest scope consistent with the following claims and the principles and novel features disclosed herein.

While various aspects and embodiments have been disclosed, other aspects and embodiments are contemplated. The various aspects and embodiments disclosed are for purposes of illustration and are not intended to be limiting, with the true scope and spirit being indicated by the following claims.

What we claim is:

1. A method of improving dose predictions of a first dose deposition model using an artificial intelligence model thereby enhancing radiation treatment for a patient, the method comprising:

receiving, by a processor, a medical image of an anatomical region of a patient from a database or a radiotherapy machine through a network;

determining, by the processor, an initial dose deposition of the anatomical region using the medical image and determined by the first dose deposition model indicating a minimum dose deposition;

determining, by the processor, an adjusted dose deposition for the medical image corresponding to an increased accuracy of the initial dose deposition using the medical image and determined by a second dose deposition model, wherein determining the adjusted dose deposition comprises removing one or more artifacts corresponding to the medical image;

training, by the processor, the artificial intelligence model to determine simulated adjusted dose depositions using the initial dose deposition, the adjusted dose deposition, and a set of training medical images, each training medical image having a corresponding first training dose deposition determined by the first dose deposition model and an adjusted training dose deposition determined by the second dose deposition model;

generating, by the processor, a simulated adjusted dose deposition by applying the trained artificial intelligence model; and adjusting, by the processor, at least one configuration radiation parameters of the radiotherapy machine based on the simulated adjusted dose deposition for the patient.

2. The method of claim 1, wherein the first dose deposition model determines a flux distribution, abstracting a dose reaction rate with the anatomical region of the patient.

3. The method of claim 1, wherein the second dose deposition model employs a nondeterministic particle behavior simulator and/or direct dose measurements.

4. The method of claim 1, wherein the minimum dose deposition determined using the first dose deposition model is adjusted using the artificial intelligence model.

5. The method of claim 1, wherein the artificial intelligence model is a neural network.

6. The method of claim 1, wherein the set of training medical images and corresponding first training dose deposition determined by the first dose deposition model and the adjusted training dose deposition determined by the second dose deposition model corresponds to a particular anatomical region.

7. The method of claim 1, wherein the set of training medical images and corresponding first training dose deposition determined by the first dose deposition model and the adjusted training dose deposition determined by the second dose deposition model corresponds to a particular clinician.

8. The method of claim 1, wherein the set of training medical images and corresponding first training dose deposition determined by the first dose deposition model and the adjusted training dose deposition determined by the second dose deposition model corresponds to a particular radiotherapy machine.

9. The method of claim 1, wherein the adjusted training dose deposition is modified according to a preference of a medical professional, the artificial intelligence model being trained to simulate the adjusted training dose deposition determined by the second dose deposition model and modified according to the preference of the medical professional.

10. A system for improving dose predictions of a first dose deposition model using an artificial intelligence model thereby enhancing radiation treatment for a patient, the system comprising:

a server comprising a processor and a non-transitory computer-readable medium containing instructions that when executed by the processor cause the processor to perform operations comprising:

receiving a medical image of an anatomical region of a patient from a database or a radiotherapy machine through a network;

determining an initial dose deposition of the anatomical region using the medical image and determined by the first dose deposition model indicating a minimum dose deposition;

determining an adjusted dose deposition for the medical image corresponding to an increased accuracy of the initial dose deposition using the medical image and determined by a second dose deposition model, wherein determining the adjusted dose deposition comprises removing one or more artifacts corresponding to the medical image;

training the artificial intelligence model to determine simulated adjusted dose depositions using the initial dose deposition, the adjusted dose deposition, and a set of training medical images, each training medical image having a corresponding first training dose deposition determined by the first dose deposition model and an adjusted training dose deposition determined by the second dose deposition model;

generating a simulated adjusted dose deposition by applying the trained artificial intelligence model; and adjusting at least one configuration radiation parameters of the radiotherapy machine based on the simulated adjusted dose deposition for the patient.

11. The system according to claim 10, wherein the first dose deposition model determines a flux distribution abstracting a dose reaction rate with an anatomical region of the patient.

12. The system according to claim 10, wherein the second dose deposition model employs a nondeterministic particle behavior simulator and/or direct dose measurements.

13. The system according to claim 10, wherein the minimum dose deposition determined using the first dose deposition model is adjusted using the artificial intelligence model.

14. The system according to claim 10, wherein the artificial intelligence model is a neural network.

15. The system according to claim 10, wherein the set of training medical images and corresponding first training dose deposition determined by the first dose deposition model and the adjusted training dose deposition determined by the second dose deposition model corresponds to a particular anatomical region.

16. The system according to claim 10, wherein the set of training medical images and corresponding first training dose deposition determined by the first dose deposition model and the adjusted training dose deposition determined by the second dose deposition model corresponds to a particular clinician.

17. The system according to claim 10, wherein the set of training medical images and corresponding first training dose deposition determined by the first dose deposition model and the adjusted training dose deposition determined by the second dose deposition model corresponds to a particular radiotherapy machine.

18. The system according to claim 10, wherein the adjusted training dose deposition is modified according to a preference of a medical professional, the artificial intelligence model being trained to simulate the adjusted training dose deposition determined by the second dose deposition model and modified according to the preference of the medical professional.

* * * * *